United States Patent [19]

Cooperman et al.

[11] 4,220,581
[45] Sep. 2, 1980

[54] CASTOR BASED QUATERNARIES

[75] Inventors: Murray C. Cooperman, East Windsor; Francis Duneczky, Westfield; Francis C. Naughton, Mountainside; Robert W. White, Califon, all of N.J.

[73] Assignee: NL Industries, Inc., New York, N.Y.

[21] Appl. No.: 812,098

[22] Filed: Jul. 1, 1977

[51] Int. Cl.$^2$ .......................... C08H 3/00; C09F 5/00; A61K 7/06; D06B 3/00
[52] U.S. Cl. ............................. 260/402.5; 260/404.5; 260/403; 424/70; 8/115.6; 8/188; 8/127.6
[58] Field of Search ................ 260/567.6 M, 567.6 R, 260/404.5 Q, 402.5, 403; 424/70

[56] References Cited

U.S. PATENT DOCUMENTS

| 2,125,901 | 8/1938 | Gwynant et al. | 260/567.6 M |
| 2,459,088 | 1/1949 | Moss et al. | 260/567.6 M |
| 2,695,314 | 11/1954 | Kosmin | 260/567.6 M |
| 2,963,339 | 12/1960 | Keller | 260/404.5 Q |
| 3,180,870 | 4/1965 | Spitzer et al. | 260/404.5 Q |
| 3,221,042 | 11/1965 | Margot | 260/567.6 M |
| 3,324,091 | 6/1967 | Savides | 260/567.6 M |
| 4,012,398 | 3/1977 | Conner et al. | 260/404.5 Q |
| 4,069,347 | 1/1978 | McCarthy et al. | 424/70 |

Primary Examiner—Bernard Helfin
Assistant Examiner—James H. Reamer
Attorney, Agent, or Firm—Gary M. Nath; Malcolm M. Sutherland

[57] ABSTRACT

The castor based quaternaries of the instant invention are prepared by condensing a castor fatty acid with the amino protons of a diamine containing a tertiary amino group at one end to form an intermediate product and then quaternizing the intermediate product.

9 Claims, No Drawings

CASTOR BASED QUATERNARIES

BACKGROUND OF THE INVENTION

The cationic quaternary type of fatty derivation based on coconut, soybean or tallow fats has been the basis for the development of textile softening agents and/or cosmetic ingredients and other industrial uses. A typical tallow derived softening agent is the distearyl dimethyl quaternary ammonium chloride structure as indicated:

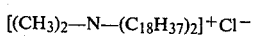

$$[(CH_3)_2-N-(C_{18}H_{37})_2]^+ Cl^-$$

This is usually offered as a paste form at 75% solids in isopropanol or in lower dilutions in a mixture of isopropanol and water. This product has a very limited degree of water solubility, and exhibits irritation properties. Alternate methods employ an amide route including ethoxylation to develop other tallow based derivatives of higher polarity for improved water solubility, see U.S. Pat. No. 2,459,088. This is illustrated for another stearyl type quaternary:

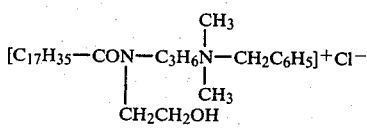

$$[C_{17}H_{35}-CON-C_3H_6N-CH_2C_6H_5]^+ Cl^-$$
with $CH_3$ and $CH_2CH_2OH$ substituents Compounds of this type have improved water solubility and softening properties. However, they are also fairly irritating. One recent development is the utilization of Lanolin fatty acids as a route for improving the irritation properties but this occurs at the expense of water solubility. A typical quaternary of this technology is illustrated:

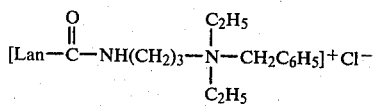

$$[Lan-\overset{O}{\underset{\|}{C}}-NH(CH_2)_3-\underset{\underset{C_2H_5}{|}}{\overset{\overset{C_2H_5}{|}}{N}}-CH_2C_6H_5]^+ Cl^-$$

where Lan is defined as the mixed higher molecular weight fatty acids derived from Lanolin or wool fat.

In contrast to the prior art, the instant invention is directed to quaternized castor fatty acid based amido-amines prepared by (1) condensing a castor fatty acid with the amido protons of a diamine containing a tertiary amino group at one end to form a fatty amido-amine intermediate and then (2) quaternizing this intermediate with a quaternizing agent, and to these compounds used as softeners and fixatives. This invention takes advantage of the unique emollient and lubricating properties of the castor fatty acids which contain hydroxy groups capable of imparting extra softening, e.g. in textiles, and fixative properties so that the compounds do not easily wash out. Additionally the compounds have a high degree of water solubility and are not irritating. These properties are particularly useful in textile and cosmetic formulations such as fabric softeners, hair shampoos, etc. Unique cosmetic properties are also associated with compounds based upon castor based fattty acids which do not contain the hydroxy group and these compounds are included in this disclosure.

The castor based fatty acids preferably employed in the instant invention are ricinoleic acid, 12-hydroxystearic acid, and ethoxylated or propoxylated derivatives of ricinoleic acid or 12-hydroxystearic acid. Undecylenic acid, heptanoic acid and DCO fatty acids also can be used to produce compounds of this invention.

The general formula for the amido-amine intermediate condensation product derived from the fatty acid is illustrated by the following typical reaction:

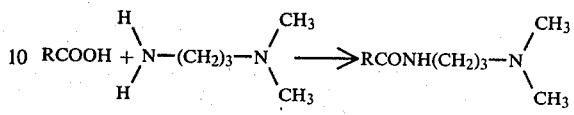

$$RCOOH + \underset{H}{\overset{H}{\diagdown}}N-(CH_2)_3-N\underset{CH_3}{\overset{CH_3}{\diagup}} \longrightarrow RCONH(CH_2)_3-N\underset{CH_3}{\overset{CH_3}{\diagup}}$$

In general, amines having the formula:

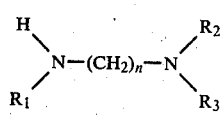

$$\underset{R_1}{\overset{H}{\diagdown}}N-(CH_2)_n-N\underset{R_3}{\overset{R_2}{\diagup}}$$

where
n = 1 to 10;
$R_1$ = H, saturated alkyl groups of $CH_3$ through $C_{10}H_{21}$, or alkenyl groups of $C_2H_4$ through $C_{10}H_{20}$; and, $R_2$ and $R_3$ can be the same as $R_1 \cdot R_1$, $R_2$ and $R_3$ do not have to be the same but are independently selected. Substituted aminopropylamines where n is three, particularly alkyl substituted, e.g. dialkyl substituted aminopropylamines are a preferred class of amines. N,N-dimethylaminopropylamine having the formula:

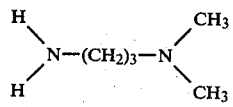

$$\underset{H}{\overset{H}{\diagdown}}N-(CH_2)_3-N\underset{CH_3}{\overset{CH_3}{\diagup}}$$

is typical.

The quaternizing agents which can be used in this invention include benzyl chloride or alkyl chlorides, bromides, phosphates and sulfates, such as dimethyl sulfate, dimethyl bromide and diethylsulfate.

The quaternary compounds of this invention can be represented by the formula:

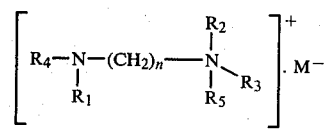

$$\left[R_4-\underset{R_1}{\overset{|}{N}}-(CH_2)_n-\underset{R_5}{\overset{\overset{R_2}{|}}{N}}_{R_3}\right]^+ \cdot M^-$$

where: n, $R_1$, $R_2$ and $R_3$ have the meanings described above; $R_4$ = 12-hydroxystearyl, ricinoleyl, 12-(2-hydroxypropyloxy) stearyl, 12-(2-hydroxyethyloxy) stearyl, 12-(2-hydroxyethyloxy)oleyl 12-(2-hydroxypropyloxy) oleyl, undecylenyl, heptanoyl, or 9, 11-linoleyl; $R_5$ = benzyl or alkyl of 1 to 3 carbon atoms; and M = chloride, bromide, phosphate or sulfate. The 12-hydroxystearic acid and ricinoleyl acid derivatives are used to produce preferred water-soluble quaternary compounds in accordance with this invention.

It is preferred to carry out the reaction in the presence of a solvent such as, for example, propylene glycol or isopropanol. Although various amounts of solvent can be employed, it has been found that about 70-75% by weight is preferred. The reactions can be carried out without a solvent, however, gelatinous end products may result which is generally undesirable.

The reactions can be carried out at various temperatures; however, temperatures from about 50° to 90° C. are most satisfactory. The following general reaction illustrating the quaternization of the amido-amine intermediate with benzyl chloride, a preferred agent, is typical:

$RCONH(CH_2)_3N(CH_3)_2 +$

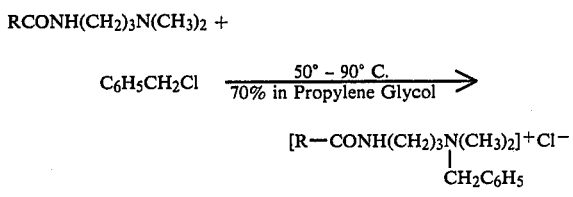

$$[R-CONH(CH_2)_3\underset{\underset{CH_2C_6H_5}{|}}{N}(CH_3)_2]^+Cl^-$$

In order to describe the instant invention more thoroughly, the following examples are presented:

EXAMPLE 1

Production of γ-Ricinoleamidopropyl-dimethyl-benzyl ammonium chloride:

(a) Stage 1: Preparation of γ-Ricinoleamidopropyl-dimethylamine.

383 g (3.75 moles) of N,N-dimethylaminopropylamine were mixed with 1,043 g of commercial ricinoleic acid (3.5 moles) and heated to 180°–185° C. in a 5 liter reactor. The water of reaction is removed and the reaction is continued until a minimum acid value is attained. The product was then vacuum dried at 100°–105° C. at 50 mm vacuum. The amido-amide intermediate, γ-Ricinoleamidopropyldimethylamine, had the following properties:

| Amine Value | 146 |
|---|---|
| Acid Value | 4.5 |
| Neutralization Equiv. | 383 (theory 382) |
| Appearance | Amber Clear Liquid |
| Yield g. | 1274 |

(b) Stage 2: Preparation of γ-Ricinoleamidopropyl-dimethylbenzyl ammonium chloride.

1,266 g (3.305 moles) of the amido-amine intermediate, γ-Ricinoleamidopropyl-dimethylamine, were mixed with 430 g of benzyl chloride (3.386 moles), 712 g propylene glycol and 48 g sodium bicarbonate. The mixture contained 72% solids. The mixture was heated to 70°–80° C. and allowed to react for 3 hours. Samples were removed periodically to determine the percentages of free amine and amine hydrochloride. When the minimum amounts were obtained, the batch was cooled to 25° C. and filtered to remove the inorganic salts. The product had the following properties:

| Free Amine, % | 2.99 |
|---|---|
| Amine Hydrochloride, % | 0.13 |
| Spec. Grav., 25° C. | 1.022 |
| Density, lbs./gal. | 8.48 |
| Ash, % | 0 |
| Viscosity, Strokes, 25° C. | 15.3 |
| Appearance | Amber Clear Liquid |
| Yield g | 2,333 |
| pH, 10% Aqueous Soln. | 6.9–7.1 |

γ-Ricinoleamidopropyl-dimethyl-benzyl ammonium chloride (Compound 1) is utilized in hair use products and textile softening agents to impart extra softening and fixative properties. The following formulations are typical:

| Creme Rinse: | |
|---|---|
| Lauryl dimethyl amine oxide | 1–3 parts |
| Compound 1, 70% active cationic | 3–4 parts |
| Lanolin alcohol ethoxylates | 2–4 parts |
| Water | q.s. |
| Shampoo: | |
| Sodium lauryl ether sulfate, 40% active | 25–30 parts |
| Coco diethanol amide | 3.5–5 parts |
| Compound 1, 70% active cationic | 2–4.0 parts |
| Wilson's Protein WSP X-250 | 2–4.0 parts |
| Preservative | 0.1–0.2 parts |
| EDTA | 0.1–0.25 parts |
| Water | q.s. to 100 |

EXAMPLE 2

Production of γ-12-Hydroxystearamidopropyl-dimethylbenzyl ammonium chloride:

(a) Stage 1: Preparation of γ-12-Hydroxystearamidopropyl-dimethylamine.

655 g (6.42 moles) of N,N-dimethylaminopropylamine were mixed with 1800 g (6 moles) of 12-hydroxystearic acid and heated to 180°–185° C. in a 5 liter reactor. The water of reaction is removed and the reaction is continued until a minimum acid value is obtained. The product was then vacuum dried at 100°–105° C. at 50 mm vacuum. The amido-amide intermediate product, γ-12-Hydroxystearamidopropyl-dimethylamine, had the following properties:

| Amine Value | 144 |
|---|---|
| Acid Value | 5.1 |
| Neutralization Equiv. | 389 (theory 384) |
| Appearance | Light Tan Wax |
| Yield g | 2248 |

(b) Stage 2: Preparation of γ-12-Hydroxystearamidopropyldimethyl-benzyl ammonium chloride.

1751 g (4.5 moles) of this intermediate product, γ-12-Hydroxystearamidopropyl-dimethylamine, were mixed with 587 g of benzyl chloride (4.62 moles), 981 g propylene glycol and 66 g sodium bicarbonate. The mixture contained 72% solids. The mixture was heated to 70°–80° C. and allowed to react for 5 hours. Samples were removed periodically to determine the percentages of free amine and amine hydrochloride. When the minimum amounts were obtained, the warmed product was filtered to remove the inorganic salts. The product has the following properties:

| Free Amine, % | 2.61 |
|---|---|
| Amine Hydrochloride, % | 0.16 |
| Spec. Grav., 25° C. | 1.012 |
| Density, lbs./gal. | 8.43 |
| Melting Point, °C. | 66 |
| Ash, % | 0 |
| Viscosity, Stokes, 100° C. | 0.4 |
| Appearance | Soft White Wax |
| Yield g | 3,291 |
| pH, 10% Aqueous Soln. | 7.4–7.5 |

γ-12-Hydroxystearamidopropyl-dimethyl-benzyl ammonium chloride (Compound 2) is utilized in hair care products, having the formulations of Example 1, and textile softening agents. The following textile formulation is typical:

| Fabric Softener: | |
|---|---|
| Compound 2, 70% active cationic | 3–5 parts |
| EDTA | 0.1–0.25 parts |
| Water | q.s. to 100 parts |

EXAMPLE 3

Production of γ-10-Undecylenamidopropyl-dimethyl-benzyl ammonium chloride:

(a) Stage 1: Preparation of γ-10-Undecylenamidopropyl-dimethylamine.

956 g (9.37 moles) of N,N-dimethylaminopropylamine were mixed with 1,610 g (8.75 moles) of undecylenic acid and heated to 180°–185° C. in a 5 liter reactor. The water of reaction is removed and the reaction is continued until a minimum acid value is obtained. The product was then vaccum dried at 100°–105° C. at 50 mm vacuum. The amido-amine intermediate product, γ-10-undecylenamidopropyl-dimethylamine, had the following properties:

| Amine Value | 202 |
|---|---|
| Acid Value | 5.39 |
| Neutralization Equiv. | 273 (theory 268) |
| Appearance | Amber Clear Liquid |
| Yield g | 2,316 |

(b) Stage 2: Preparation of γ-10-Undecylenamidopropyl-dimethyl-benzyl ammonium chloride.

1706 g (6.25 moles) of γ-10-Undecylenamidopropyl-dimethylamine were mixed with 813 g. benzyl chloride (6.4 moles), 1,052 g propylene glycol, and 71 g sodium bicarbonate. The mixture contained 72% solids. The mixture was heated to 60°–80° C. and allowed to react for 2 hours. Samples were removed periodically to determine the percentages of free amine and amine hydrochloride. When the minimum amounts were obtained, the product was cooled to room temperature and filtered to remove the inorganic salts. The product had the following properties:

| Free Amine, % | 3.86 |
|---|---|
| Amine Hydrochloride, % | 0.18 |
| Spec. Grav., 25° C. | 1.033 |
| Density, lbs./gal. | 8.6 |
| Ash, % | 0 |
| Viscosity, Stokes, 25° C. | 12.9 |
| Appearance | Amber Clear Liquid |
| Yield g | 3,468 |

γ-10-Undecylenamidopropyl-dimethyl-benzyl ammonium chloride (Compound 3) is useful in the area of hair care products and laundry detergents. A typical formulation is:

| Laundry Detergent: | |
|---|---|
| Sodium Lauryl Sulfate, 30% Active | 20–25 parts |
| Sodium Lauryl Ether Sulfate, 30% Active | 20–25 parts |
| Alkylamido Sulfosuccinate, Sodium Salt, 30% Active | 3–5 parts |
| Compound 3, 70% Active Cationic | 2–3 parts |
| Nonionic Surfactant | 5–7 parts |
| EDTA, Disodium Salt | 1–2 parts |
| Calcofluor White SD | 0.1–0.2 parts |

| -continued | |
|---|---|
| Laundry Detergent: | |
| Water | q.s. to 100 parts |

EXAMPLE 4

Production of γ-9,11-Linoleamidopropyl-dimethyl-benzyl ammonium chloride.

(a) Stage 1: Preparation of γ-9,11-Linoleamidopropyldimethylamine.

383 g (3.75 moles) of N,N-dimethylaminopropylamine were mixed with 980 g (3.5 moles of DCO fatty acids and heated to 180°–185° C. in a 3 liter reactor. The water of reaction is removed, and the reaction is continued until a minimum acid value is obtained. The product was then vaccum dried at 100°–105° C. at 50 mm vacuum. The amido-amine intermediate product, γ-9,11-Linoleamidopropyl-dimethylamine, had the following properties:

| Amine Value | 162 |
|---|---|
| Acid Value | 5.93 |
| Neutralization Equiv. | 346 (theory 364) |
| Appearance | Amber Clear Liquid |
| Yield g | 1,248 |

(b) Stage 2: Preparation of γ-9,11-Linoleamidopropyl-dimethyl-benzyl ammonium chloride.

537 g (1.552 moles) of γ-9,11-Linoleamidopropyl-dimethylamine were mixed with 202 g benzyl chloride (1.591 moles), 310 g propylene glycol, and 21 g. sodium bicarbonate. The mixture contained 72% solids. The mixture was heated to 70°–80° C. and allowed to react for 2½ hours. Samples were removed periodically to determine the percentages of free amine and amine hydrochloride. When the minimum amounts were obtained, the product was cooled to room temperature (25° C.) and filtered to remove the inorganic salts. The product had the following properties:

| Free Amine, % | 2.95 |
|---|---|
| Amine Hydrochloride, % | 0.37 |
| Spec. Gravity, 25° C. | 1.014 |
| Density, lbs./gal. | 8.41 |
| Ash, % | 0.01 |
| Viscosity, Stokes, 25° C. | 11.14 |
| Appearance | Amber Clear Liquid |
| Yield g | 1,023 |
| pH, 10% Aqueous | 6.1–6.2 |

γ-9,11-Linoleamidopropyl-dimethyl-benzyl ammonium chloride (Compound 4) is useful in the area of hair care products. A typical formulation is given:

| Wave Set, or Setting Lotion: | |
|---|---|
| Resyn 28-2930 | 1.75–2.25 parts |
| AMP | 0.18–0.25 parts |
| Compound 4, 70% Active Cationic | 2.0–4.0 parts |
| Nonionic Surfactant | 0.1–0.2 parts |
| Water | q.s. to 100 parts |

EXAMPLE 5

Production of γ-Heptanoamidopropyl-dimethyl-benzyl ammonium chloride.

(a) Stage 1: Preparation of γ-Heptanoamidopropyl-dimethylamine.

383 g (3.75 moles) of N,N-dimethylaminopropylamine were mixed with 445 g (3.5 moles) of heptanoic acid and heated to 180°–185° C. in a 2 liter reactor. The water of reaction is removed, and the reaction is continued until a minimum acid value is obtained. The product was then vacuum dried at 100°–105° C. at 50 mm vacuum. The amido-amine intermediate product, γ-Heptanoamidopropyl-dimethylamine, had the following properties:

| Amine Value | 256 (theory 262) |
|---|---|
| Acid Value | 6.3 |
| Neutralization Equiv. | 219 (theory 214) |
| Appearance | Amber Clear Liquid |
| Yield g | 678 |

(b) Stage 2: Preparation of γ-Heptanoamidopropyl-dimethyl-benzyl ammonium chloride.

438 (2.0 moles) of γ-Heptanoamidopropyl dimethylamine were mixed with 260 g benzyl chloride (2.05 moles), 291 g propylene glycol, and 10 g sodium bicarbonate. The mixture contained 72% solids. The mixture was heated to 60°–65° C. and allowed to react for 1 hour. Samples were removed periodically to determine the percentages of free amine and amine hydrochloride. When the minimum amounts were obtained, the product was cooled to 40° C. and filtered to remove the inorganic salts. The product had the following properties:

| Free Amine, % | 1.75 |
|---|---|
| Amine Hydrochloride, % | 0.38 |
| Ash, % | .02 |
| Gardner Holdt Viscosity, 25° C. | Y + ¼ |
| Appearance | Amber Clear Liquid |
| Yield g | 944 |

EXAMPLES 6–14

The following quaternary compounds are produced by the procedure described in the preceeding examples using the described amines and acids.

EXAMPLE 15

Compounds wherein $R_5$ is methyl are produced by substituting methyl chloride for benzyl chloride in the process of Examples 1 to 5. Similarly compounds where $R_5$ is ethyl and M is sulfate are produced substituting diethyl sulfate for benzyl chloride.

EXAMPLE 16

The quaternary compounds produced in accordance with Examples 6 through 15 are substituted for compounds 1, 2, 3 and 4 to produce fabric softeners, laundry detergents, cream rinses and hair shampoos of the formulae set forth in Examples 1 through 4.

It is claimed:

1. A quaternary compound of the formula:

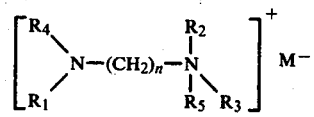

wherein: $R_1$, $R_2$ and $R_3$ are independently selected from the group consisting of hydrogen, alkyl of about 1 to 10 carbon atoms and alkenyl of up to about 10 carbon atoms; n is an integer of about 1 to 10; $R_4$ is selected from the group consisting of 12-hydroxystearyl; ricinoleyl, 12-(2-hydroxyethyloxy)stearyl, 12-(2-hydroxyethyloxy) oleyl, 12-(2-hydroxypropyloxy) stearyl and 12-(2-hydroxy propyloxy) oleyl; $R_5$ is selected from the group consisting of benzyl and alkyl of about 1 to 3 carbon atoms; and M is selected from the group consisting of chloride, bromide, phosphate and sulfate.

2. A quaternary compound as defined in claim 1 wherein n is 3.

3. A quaternary compound as defined in claim 2 wherein $R_1$ is hydrogen.

4. A quaternary compound as defined in claim 3 wherein $R_4$ is 12-hydroxystearyl.

5. A quaternary compound as defined in claim 4 wherein $R_2$ and $R_3$ are methyl.

6. A quaternary compound as defined in claim 3 wherein $R_4$ is ricinoleyl.

7. A quaternary compound as defined in claim 6 wherein $R_2$ and $R_3$ are methyl.

8. γ-(ricinoleamido)propyl-dimethyl-benzyl-ammonium chloride.

9. γ-(12-hydroxystearylamido)propyl-dimethyl-benzylammonium chloride.

* * * * *

| EXAMPLE | COMPOUND | AMINE | ACID |
|---|---|---|---|
| 6 | γ(N-methyl-12-hydroxystearamido)propyl-dimethyl-benzyl-ammonium chloride | γ(N-methylamino) propyl-dimethyl-amine | 12-hydroxystearic acid (Acid No. 1) |
| 7 | 4(N-methyl-ricinoleylamido)butyl-diethyl-benzyl-ammonium chloride | 4(N-methylamino) butyl-diethyl-amine | ricinoleic acid (Acid No. 2) |
| 8 | γ(N-methyl-ricinoleylamido)propyl-didecyl-benzyl-ammonium chloride | γ(N-methylamino)propyl-didecyl-amine | No. 2 |
| 9 | 2-ricinoleylamidoethyl-dioctyl-benzyl-ammonium chloride | 2-aminoethyl-dioctyl amine | No. 2 |
| 10 | γ(N-hexyl-ricinoleylamido)propyl-propyl-methyl-benzyl-ammonium chloride | γ(N-hexylamino)propyl-propyl-methyl-amine | No. 2 |
| 11 | 9(12-(2-hydroxyethyloxy)stearamido) nonyl-dimethyl-benzyl-ammonium chloride | 9-aminononyl-dimethyl amine | 12-(2-hydroxy ethyloxy) stearic acid |
| 12 | γ-12-(2-hydroxypropyloxy)stearamido) propyl-dimethyl-benzyl-ammonium chloride | N,N-dimethylamino propylamine | 12-(2-hydroxy propyloxy)-stearic acid |
| 13 | γ-(12-hydroxystearamido)propyl-dipropenyl-benzyl-ammonium chloride | N,N-dipropenylamino propylamine | 12-hydroxy stearic acid |
| 14 | γ(N-methyl-ricinoleamido)propyl-diethenyl-benzyl-ammonium chloride | N,N-diethenylamino propylamine | ricinoleic acid |